US011421869B2

(12) United States Patent
Peterson

(10) Patent No.: US 11,421,869 B2
(45) Date of Patent: Aug. 23, 2022

(54) METHOD FOR REMOTELY COOLING A SCOPE-MOUNTED (DISTAL) ARTHROSCOPIC LIGHT SOURCE

(71) Applicant: Conmed Corporation, Utica, NY (US)

(72) Inventor: Eric D. Peterson, Dunedin, FL (US)

(73) Assignee: Conmed Corporation, Utica, NY (US)

(*) Notice: Subject to any disclaimer, the term of this patent is extended or adjusted under 35 U.S.C. 154(b) by 0 days.

(21) Appl. No.: 17/292,924

(22) PCT Filed: Nov. 12, 2019

(86) PCT No.: PCT/US2019/060830
§ 371 (c)(1),
(2) Date: May 11, 2021

(87) PCT Pub. No.: WO2020/102134
PCT Pub. Date: May 22, 2020

(65) Prior Publication Data
US 2022/0003401 A1    Jan. 6, 2022

Related U.S. Application Data

(60) Provisional application No. 62/760,404, filed on Nov. 13, 2018.

(51) Int. Cl.
*F21V 29/76* (2015.01)
*F21V 29/67* (2015.01)
(Continued)

(52) U.S. Cl.
CPC ............ *F21V 29/76* (2015.01); *F21V 23/001* (2013.01); *F21V 29/673* (2015.01);
(Continued)

(58) Field of Classification Search
CPC ...... F21V 29/76; F21V 29/673; F21V 23/001; F21V 33/0068
(Continued)

(56) References Cited

U.S. PATENT DOCUMENTS

| 4,321,659 A | * | 3/1982 | Wheeler | F21V 29/673 |
| | | | | 362/293 |
| 8,109,981 B2 | * | 2/2012 | Gertner | A61N 5/0624 |
| | | | | 607/88 |

(Continued)

FOREIGN PATENT DOCUMENTS

CA    2752469    8/2009

OTHER PUBLICATIONS

International Search Report Form PCT/ISA/220, International Application No. PCT/US2019/060830, pp. 1-8, dated Jan. 29, 2020.

*Primary Examiner* — Bryon T Gyllstrom
(74) *Attorney, Agent, or Firm* — Bond, Schoeneck & King, PLLC; Frederick J. M. Price

(57) ABSTRACT

A surgical light source system for cooling high-powered arthroscopic light emitters. The surgical light source system includes a housing having a proximal end and a distal end with a tube connected to the proximal end. The system also includes a light source at the distal end of the housing which is connected to a remote power source. The system has a plurality of fins extending around the light source within the housing and a remote fan connected to the tube. The remote fan is adapted to draw air across the fins, forming a heatsink within the housing.

16 Claims, 4 Drawing Sheets

(51) Int. Cl.
  *F21V 23/00*   (2015.01)
  *F21V 33/00*   (2006.01)
  *F21Y 115/10*  (2016.01)
  *F21W 131/20*  (2006.01)

(52) U.S. Cl.
  CPC ..... *F21V 33/0068* (2013.01); *F21W 2131/20* (2013.01); *F21Y 2115/10* (2016.08)

(58) Field of Classification Search
  USPC ........................................................ 362/572
  See application file for complete search history.

(56) References Cited

U.S. PATENT DOCUMENTS

| | | | |
|---|---|---|---|
| 10,141,489 B1 * | 11/2018 | Nakamura | F21V 29/70 |
| 2002/0182563 A1 * | 12/2002 | Boutoussov | F21V 29/83 |
| | | | 433/29 |
| 2013/0344454 A1 * | 12/2013 | Nath | A61N 5/0616 |
| | | | 433/29 |
| 2014/0233230 A1 * | 8/2014 | Chen | F21K 9/60 |
| | | | 362/235 |
| 2015/0159851 A1 * | 6/2015 | Li | F21V 23/009 |
| | | | 362/294 |
| 2019/0021583 A1 * | 1/2019 | Yoshida | F21V 29/673 |

* cited by examiner

METHOD FOR REMOTELY COOLING A SCOPE-MOUNTED (DISTAL) ARTHROSCOPIC LIGHT SOURCE

CROSS-REFERENCES TO RELATED APPLICATIONS

This application is a national stage application under 35 U.S.C. 371 based on international patent application PCT/US19/6083 filed on Nov. 12, 2019, which claims priority to U.S. Provisional Patent Application Ser. No. 62/760,404 filed on Nov. 13, 2018, the entireties of which are incorporated herein by reference.

BACKGROUND OF THE INVENTION

1. Field of the Invention

The present invention relates to a surgical system and, more particularly, to a surgical light source system for cooling high-powered arthroscopic light emitters.

2. Description of Related Art

Typically, light at surgical sites is limited due to the heat that is emitted. Light emitters can generate a high level of heat near the patent and the surgeon. Such a high level of heat puts both the patient and the surgeon at risk for discomfort, overheating, and burns. Currently, a fiber optic light guide is attached to a proximal end of the arthroscope. However, the fiber optic light guide suffers from wear, progressive fiber breakage, and deterioration of fiber end faces over multiple cleaning and sterilization cycles. Constant replacement of fiber optic light guides and their component parts can become expensive and burdensome.

Therefore, there is a need for a disposable surgical light source system that cools high-powered light emitters used in arthroscopic surgical procedures.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The present disclosure is directed to a surgical light source system for cooling high-powered arthroscopic light emitters. According to an aspect, the present invention is a surgical light source system. The surgical light source system includes a housing having a proximal end and a distal end with a tube connected to the proximal end. The system also includes a light source at the distal end of the housing which is connected to a remote power source. The system has a plurality of fins extending around the light source within the housing and a remote fan connected to the tube. The remote fan is adapted to draw air across the fins, forming a heatsink within the housing.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Figure 1:
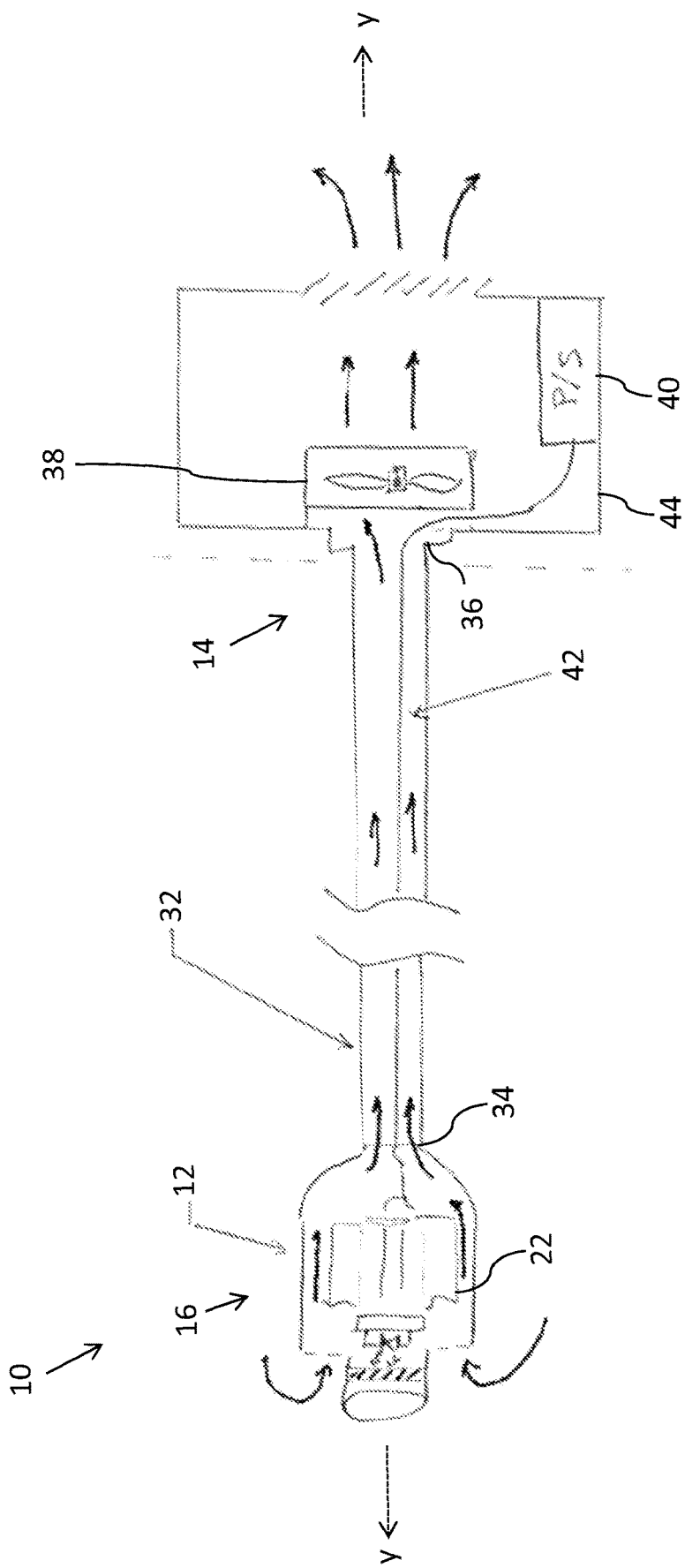
FIG. 1 is a side sectional view schematic representation of a surgical light source system, according to an embodiment.
Figure 4:
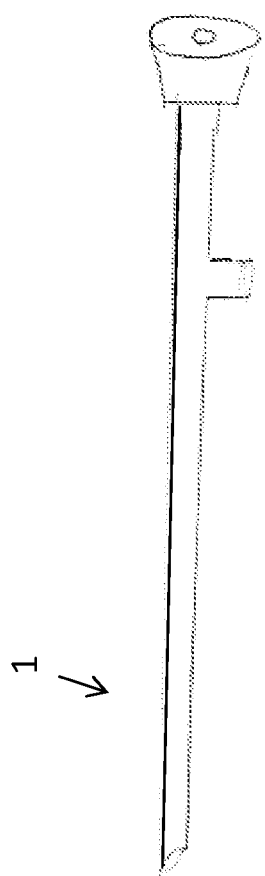
FIG. 4 is a side view schematic representation of a traditional arthroscope.

Referring now to the drawings, wherein like reference numerals refer to like parts throughout, there is seen in FIG. 1, a side sectional view schematic representation of a surgical light source system 10, according to an embodiment. The distal end 16 of the surgical light source system 10 is configured to attach to a traditional arthroscope 1 such as that shown in FIG. 4 (by any traditional means, as should be understood by a person of ordinary skill in the art in conjunction with a review of this disclosure). The system 10 includes a proximal end 14 and a distal end 16 with a housing 12 at the distal end 16. In a preferred embodiment, the housing 12 is formed of a lightweight, plastic shell. For example, the housing 12 is a circular or cylindrical shell, as shown in FIG. 1. The housing 12 is configured for mounting near the distal end of any arthroscope.

Figure 2:
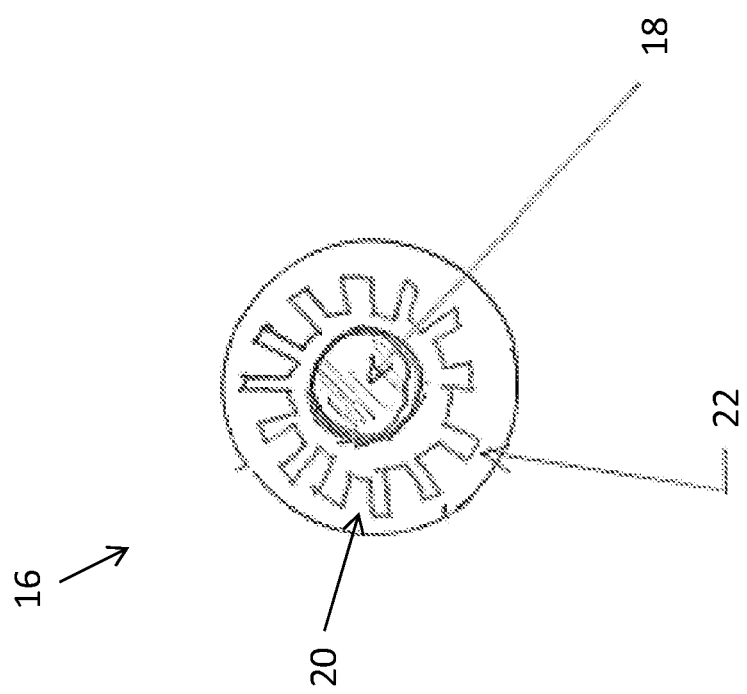
FIG. 2 is a front view schematic representation of an uncovered distal end of the surgical light source system, according to an embodiment.

Turning now to FIG. 2, there is shown a front view schematic representation of an uncovered distal end 16 of the surgical light source system 10, according to an embodiment. The distal end 16 of the system 10 comprises a light source 18 (i.e., a lens). In the depicted embodiment, the light source 18 is a circular LED light. Specifically, the light source 18 is a COB (chip-on-board) LED light that is mounted on the distal end 16 of the system 10. The distal end of 16 is a universal optical connector fitted and bonded to housing 12 (as should be understood by a person of ordinary skill in the art in conjunction with a review of this disclosure). As shown in FIG. 2, the distal end 16 of the system 10 additionally comprises a radially finned anodized aluminum heatsink 20. The radially finned heatsink 20 is created by a plurality of cooling fins 22 within the housing 12. In the depicted embodiment, the cooling fins 22 extend radially around the light source 22. As shown in FIG. 1, each of the cooling fins 22 extend in a plane that is parallel or substantially aligned with a central longitudinal axis y-y extending through the length of the system 10. The cooling functionality of the radially finned heatsink 20 is described in detail below.

Figure 3:
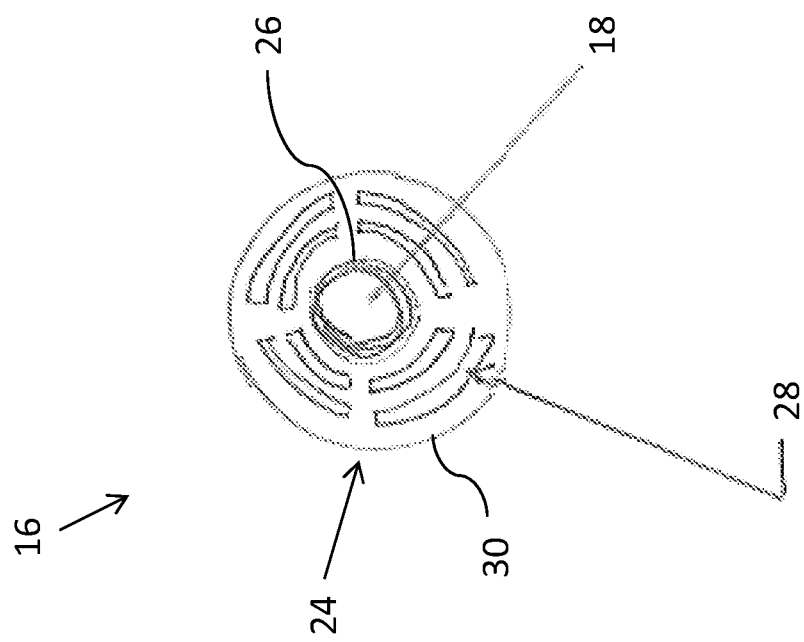
FIG. 3 is a front view schematic representation of a covered distal end of the surgical light source system, according to an embodiment.

Referring now to FIG. 3, there is shown a front view schematic representation of a covered distal end 16 of the surgical light source system 10, according to an embodiment. In use, the distal end 16 of the system 10 comprises a cap 24 or other similar covering. The cap 24 is shown in FIG. 3 extending over the light source 18 and the radial cooling fins 22 in FIG. 2. In the depicted embodiment, the cap 24 comprises a circular, central aperture 26. The aperture 26 is sized and configured to extend around the light source 18. In an embodiment, the central aperture 26 is substantially aligned with the light source 18 such that the cap 24 does not obscure light emitted by the light source 18.

Still referring to FIG. 3, the cap 24 also comprises a plurality of cooling vents 28. In the depicted embodiment, the cooling vents 28 are slots that extend through the cap 24. As also shown, the cooling vents 24 extend radially around the circular, central aperture 26. The cooling vents 28 in FIG. 3 are arranged in concentric patterns such that there are multiple cooling vents 28 between the central aperture 26 and an outer circumference 30 of the cap 24. The cooling vents 28 allow for air to flow to the radially finned heatsink 20, as described in detail below.

Referring back to FIG. 1, the housing 12 is connected to a tube 32. In the depicted embodiment, the tube 32 is a length of polyethylene tubing. The tube 32 has a distal end 34 connected to the housing 12 and a proximal end 36 connected to a fan 38. In a preferred embodiment, the fan 38 is remotely mounted to the proximal end 36 of the tube 32 such that during a surgical procedure, the fan 38 is located at a distance from the surgical site (i.e., a distance from the patient and the surgeon).

In use, the fan 38 operates to pull and draw air proximally away from the housing 12, as shown in FIG. 1. In doing so, cool air from the environment is pulled through the cooling vents 28 in the cap 24. The fan 38 continues to draw cool air through the housing 12 and across the radial cooling fins 22 (at the radially finned heatsink 20). The air is then drawn through the tube 32 to the fan 38 where it is expelled from the system 10, as shown.

Still referring to FIG. 1, the light source 18 (and, in some embodiments, the fan 38) are powered by a remote power source 40. In the depicted embodiment, the power source 40 is connected to a power wire 42. Specifically, the power wire 42 attaches to a pogo-pin connector (not shown) at the power source 40 of the system 10. The power wire 42 extends through the tube 32 to the light source 18. As mentioned and shown in FIG. 1, the power source 40 is a remote power source such that it is removed from the housing 12. The remote power source 40 can be a remote power cube, console, or a looking glass display.

The power source 40 not only provides power to the light source 18 but provides a means for adjusting the illuminance of the light source 18. In particular, the illuminance of the light source 18 is adjustable by varying the output current from the power source 40. The fan 38 and the power source 40 can be contained within a shared housing 44 remote from the surgical site, as shown in FIG. 1. The shared housing 44 may have a vent 46 or other similar element for expelling air drawn from the tube 32 by the fan 38.

Therefore, the system 10 has a remotely located power source 40 which energizes the distal high-power light source 18 and allows for a managed airflow path for cooling. This mitigates mechanical challenges associated with actively cooling the system 10 at the light source 18. Further, having a remote fan 38 and power source 40 reduces weight at the distal end 16 of the system 10 and significantly increases luminosity. With the present system 10, the light source 18 can be within millimeters of the arthroscope, eliminating the illuminance loss and chromatic aberrations of an optical fiber light guide traditionally used with arthroscopes. The present system 10 replaces the need for an optical fiber light guide, which also mitigates the concerns of wear, progressive fiber breakage, and deterioration of the fiber end faces over multiple cleaning and sterilization cycles. The present system 10 can be manufactured to be almost entirely disposable. The housing 12 (and components) and tube 32 can be composed of polyetheretherketone or similar heat-tolerant plastic and easily replaced.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A surgical light source system, comprising:
   a housing positioned at a distal end of the surgical light source system with a tube connected to a proximal end of the housing;
   a shared housing containing a remote fan and a remote power source;
   a light source disposed at a distal end of the housing and connected to the remote power source;
   a plurality of fins extending around the light source within the housing; and
   a remote fan connected to the tube, the remote fan being adapted to draw air across the fins, forming a heatsink within the housing.

2. The system of claim 1, further comprising a power wire connecting the light source to the remote power source.

3. The system of claim 2, wherein the power wire extends through the tube.

4. The system of claim 1, further comprising a cap extending over the distal end of the housing.

5. The system of claim 4, wherein the cap has a central aperture substantially aligned with the light source.

6. The system of claim 5, wherein the cap has one or more slots between the central aperture and an outer circumference of the cap, the one or more slots extending through the cap.

7. The system of claim 1, wherein the plurality of fins extend radially from the light source.

8. The system of claim 7, wherein each of the plurality of fins extends along a plane parallel to or substantially aligned with a central longitudinal axis extending through the housing.

9. The system of claim 6, wherein air current is pulled proximally by the fan through the one or more slots in the cap, across the fins, and through the tube.

10. The system of claim 1, wherein the power source emits an adjustable output current.

11. The system of claim 10, wherein increasing the output current increases an illuminance of the light source and decreasing the output current deceases the illuminance of the light source.

12. The system of claim 1, wherein the light source is a LED light.

13. The system of claim 12, wherein the light source is a COB LED light.

14. The system of claim 1, wherein the tube is composed of polyethylene tubing.

15. The system of claim 1, wherein the housing is composed of plastic.

16. The system of claim 1, wherein the housing is cylindrical.

* * * * *